| United States Patent [19] | [11] Patent Number: 4,959,308 |
|---|---|
| Ogden | [45] Date of Patent: Sep. 25, 1990 |

[54] IMMUNOASSAY FOR ANTIBODIES BINDING PLATELETS

[75] Inventor: Daryl M. Ogden, Houston, Tex.

[73] Assignee: Board of Regents, The University of Texas System, Austin, Tex.

[21] Appl. No.: 89,884

[22] Filed: Aug. 27, 1987

[51] Int. Cl.$^5$ .................. C07K 17/00; G01N 33/543
[52] U.S. Cl. ........................................... 435/7; 424/11; 427/2; 436/501; 436/506; 436/518; 436/530; 436/531; 436/543; 530/395; 530/810; 530/814; 530/815; 530/829
[58] Field of Search ......................... 424/11; 435/2, 7; 436/501, 506, 518, 543, 530, 531; 427/2; 530/395, 810, 814, 815, 829

[56] References Cited

U.S. PATENT DOCUMENTS

| 4,275,053 | 6/1981 | Rosenfield et al. | 436/531 |
|---|---|---|---|
| 4,717,654 | 1/1988 | Savoca et al. | 436/518 |
| 4,810,632 | 3/1989 | McMillan | 436/507 |

FOREIGN PATENT DOCUMENTS 2027031A 2/1980 United Kingdom .

OTHER PUBLICATIONS

Steiner et al., (1986), J. Biol. Chem., 261(16):7230–35.
Kelton, J. In: Immunologic Aspects of Platelet Transfusion Technical Workshop, (1985), L. J. McCarthy and J. Menitove, eds., Ch. 2, pp. 21–47.
Petz, L., (1988), American Journal of Clinical Pathology, 90(1):114–115.
International Search Report on the Corresponding PCT Application.
Ogden et al., (1987), Journal of Immunological Methods, 105(1):63–70.
Nel et al., (1980), Br. J. Haematol, 44:281–290.
Yesus et al., (1984), Amer. J. Clin. Pathol., 81:1.
LoBuglio et al., (1983), N. Engl. J. Med., 309:459–463.
Kickler et al., (1983), Blood, 61:238–242.
Forster and Schmidt, (1983), Klin. Wochenschr., 61:165–167.
Kunicki et al., (1979), Mol. Immunol., 16:353–360.
Dutcher et al., (1981), Blood, 58:1007–1011.
Newman et al., (1981), J. Cell Biol., 90:249–253.
Newman et al., (1982), Thromb. Res., 27:221–224.
Springer et al., (1976), Proc. Natl. Acad. Sci., 73:2481–2485.
Cook et al., (1985), Hum. Immunol., 14:234–244.
Baron et al., (1975), Biochim. Biophys. Acta, 382:276–285.
Rosevear et al., (1980), Biochem., 19:4108–4115.
Hildreth, (1982), Biochem. J., 207:363–366.
Cheng et al., (1979), J. Biol. Chem., 254:2165–2167.
Beardsley et al., (1984), J. Clin. Invest., 74:1701–1707.
Heal et al., (1987), Blood, 70:23–30.
McFarland et al., (1987), Blood, 69:1425–1430.

(List continued on next page.)

Primary Examiner—Esther M. Kepplinger
Assistant Examiner—David A. Saunders
Attorney, Agent, or Firm—Arnold, White & Durkee

[57] ABSTRACT

The present invention involves a method for producing a substrate useful in a system for the detection of antibodies directed against platelet antigens. This method comprises several steps. A platelet sample of interest is initially treated with an aqueous solution comprising a dialyzable nonionic detergent. This initial treatment is under conditions to solubilize platelet components and produce a platelet lysate. Such conditions may involve treatment of a platelet sample with an aqueous solution comprising nonionic detergent at a concentration between about 0.2% and about 0.5%. Platelet antigens are most preferably solubilized for about 30 min and at about 0° C. in an aqueous solution comprising about 1 mg dialyzable nonionic detergent per mg platelet protein.

The partially purified platelet antigens resulting from these manipulations are then preferably affixed to a solid matrix. The solid matrix preferably comprises nitrocellulose paper, polystyrene or latex but may be any solid matrix suitable for the abstraction from a biological sample and/or assay of antibodies binding to the affixed purified platelet antigens.

17 Claims, 3 Drawing Sheets

OTHER PUBLICATIONS

Vos et al., (1987), *Vox Sang,* 53:162–168.
Collins et al., (1987), *Vox Sang,* 53:157–161.
Sintnicolaas et al., (1987), *Brit. J. Haematol.,* 66:363–367.
Kelton et al., (1987), *Am. J. Hemat.,* 25:299–310.
King et al., *Blood,* 68:suppl. 1, abstr. 323.
Reid et al., *Blood,* abstr. 338.
Steiner et al., *Blood,* abstr. 350.
Stricker et al., *Blood,* abstr. 352.
Steiner et al., *Blood,* abstr. 875.
MacPherson et al., (1986), *Transfusion,* 26:467–470.
Velden et al., (1986), *Brit. J. Haematol.,* 62:635–640.
Janson et al., (1960), *Hum. Immunol.,* 15:251–262.
Stricker et al., (1985), *N. Eng. J. Med.,* 313:1375–1380.
Dunstan et al., (1985), *Brit. J. Haematol.,* 61:603–609.
Murphy et al., (1985), *Brit. J. Haematol.,* 60:409–414.
Peters et al., (1985), *Brit. J. Haematol.,* 60:117–127.
Yam et al., (1984), *Brit. J. Haematol.,* 57:337–347.
Mason et al., (1984), *Brit. J. Haematol.,* 56:529–534.
Boisvert et al., (1983), *Am. J. Clin. Path,* 80:839–843.
Myers et al., (1981), *Blood,* 58:444–450.
Tamerus et al., (1983), *Blood,* 62:744–749.
Schiffer et al., (1983), *Blood,* 61:311–317.
Palfree et al., (1982), *J. Immunol. Meth.,* 52:395–408.
McMillan et al., (1982), *Brit. J. Haematol.,* 51:297–304.
Lalezari et al., (1982), *Blood,* 59:167–170.
Hecht et al., (1982), *JAMA,* 248:2301–2303.
Waters et al., (1981), *Brit. J. Haematol.,* 48:59–68.
Gould et al., (1981), *Biochem.,* 20:6776–6781.
Gudino et al., (1981), *Blood,* 57:32–37.
*Mayo Med. Labs. Comm.,* (1983), 8:No. 12.
Schmidt et al., (1980), *Blood,* 55:299–303.
Hagen et al., (1979), *Eur. J. Biochem.,* 99:9–22.
Borne et al., (1978), *Brit. J. Haematol.,* 39:195–207.
Wu et al., (1976), *J. Clin. Invest.,* 58:432–438.
Dautigny et al., (1973), *Biochim. Biophys. Acta,* 298:783–789.
McMillan et al., (1971), *Blood,* 37:316–322.
Schiffer, *Seminar on Antigen of Blood Cells and Body Fluids,* 189–208.
Sigma Chemical Company Catalog.
Ogden et al., (1986), *Hum. Immunol.,* 17:154.
Triplett, (1978), *Platelet Function,* ASCP-Press, ch 1:1–33.
Helenius et al., (1979), *Methods in Enzymology,* LVI:734–749.
Parham, (1979), *J. Biol. Chem.,* 254:8709–8712.
Stubbs et al., (1976), *Biochem. Biophys. Acta,* 425:46–56.
Lin et al., (1979), *Biochim. Biophys. Acta,* 557:179–187.
McMillan et al., (1982), *Brit. J. Haematol.,* 51:297–304.
Kahn et al., (1981), *A Seminar on Immune-Related Cell Destruction,* 151–197.
Graddick et al., (1987), *Diagnos. Clin. Immun.,* 5:82–85.
Millard et al., (1987), *Blood,* 70:1495–1499.
Immuncor advertisement.
Bangs, Seradyn commercial literature.
Blumberg, et al., (1984), *Blood,* 63:448–450.
Kao, (1988), *Transfusion,* 28:14–17.
Hechemy, et al., (1984), *Laboratory Management,* Jun. 27–35.
Hechemy, et al., (1976), *J. Clin. Microbiol.,* 4:82–86.
Dixon, et al., (1975), *N. Eng. J. Med.,* 292:230–236.
Kiefel, et al., (1987), *Blood,* 70:1722–1726.
Nurden, et al., (1975), *Nature,* 255:720–722.
Ogden, et al., *J. of Immunological Methods* 105:63–70 (1987).
PCT International Search Report for PCT/U.S. 02953.

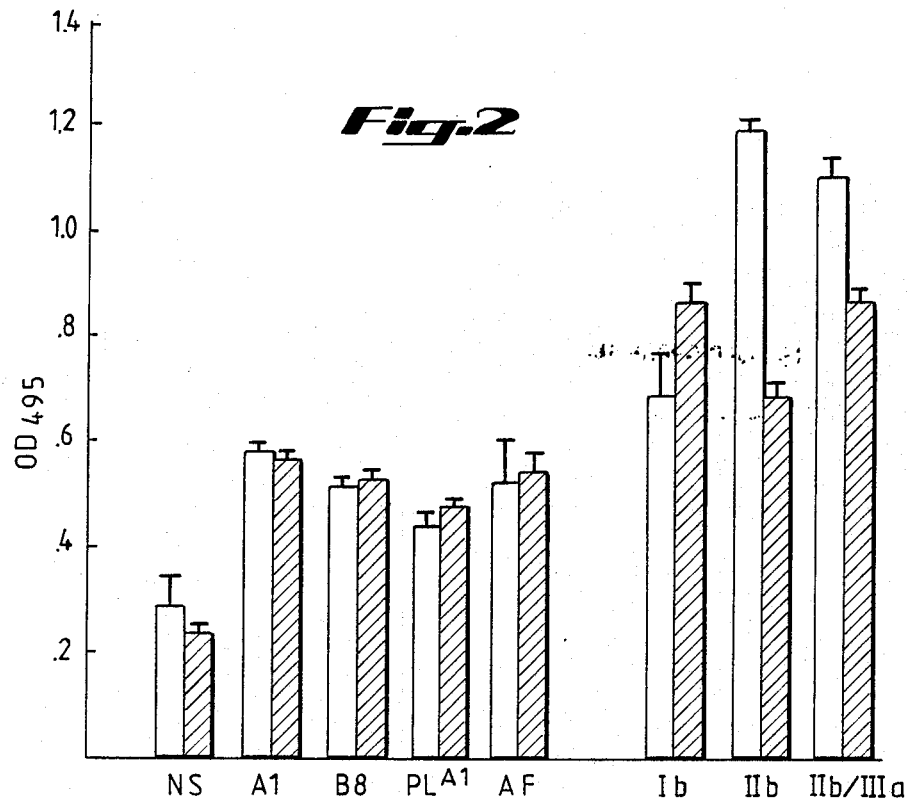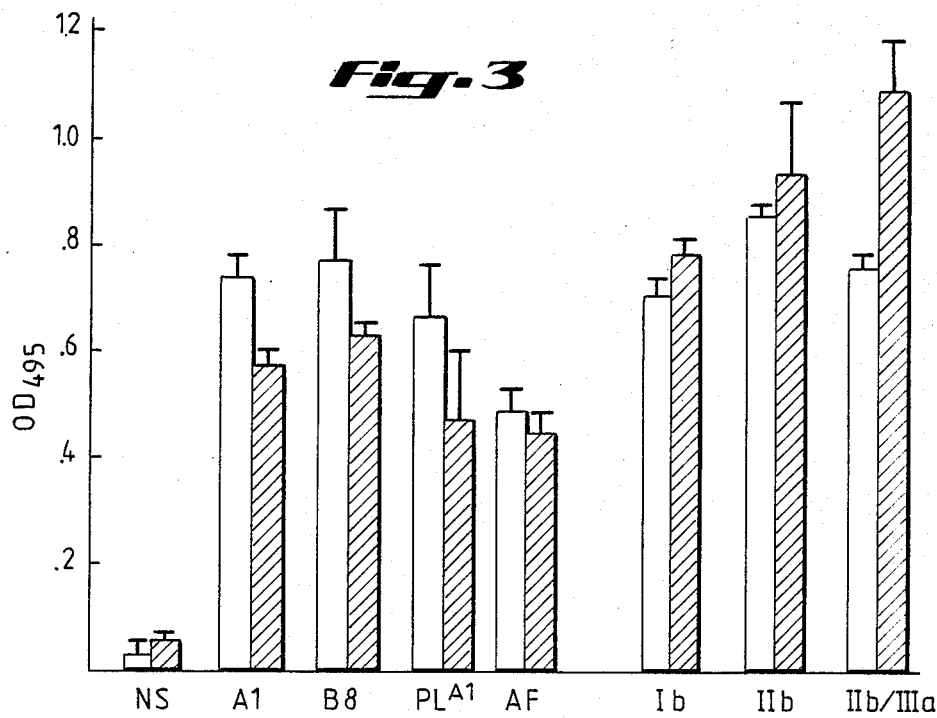

IMMUNOASSAY FOR ANTIBODIES BINDING PLATELETS

The present invention relates to a process for determination of the presence of antibodies directed against platelets. This process involves the preparation and use of solubilized platelet antigens freed of substances nonimmunospecifically binding to human IgG.

Platelet transfusion is an important hemotherapeutic supportive measure, particularly for patients undergoing bone marrow transplantation or cytoreductive chemotherapy for hematologic malignancies. Alloimmunization to antigens presented on the transfused cells becomes problematic in as many as 70% of the patients, making them refractory to further random donor platelet transfusions. Although they may initially respond to single donor, HLA-matched platelets, more recent studies have suggested that HLA matching may not reliably predict the outcome of such transfusions. This is due at least in part to the varied number of platelet membrane components that can serve as immunologic targets, some of which are still undefined. Two classes of defined platelet surface antigens exist: those also found on other cells (blood group, histocompatibility, T, and Tn antigens) and those unique to platelets.

The ABO blood group antigens (BGA) were detected on platelets more than thirty years ago. It has since been shown that these antigens are adsorbed to the surface of the platelet rather than being an intrinsic part of the membrane structure. The amount of BGA substance on platelets is proportional to the amount in the plasma. In addition, these platelet-BGA substances possess different biochemical characteristics than BGA substances present on erythrocytes. As such, transfusion with ABO-incompatible platelets causes only an initial reduction in platelet recovery, the remaining platelets surviving normally. BGA have been implicated as the target antigens responsible for transfusion failures of ABO-mismatched, HLA-matched platelets in two leukemia patients. Platelets probably do not carry any of the other BGA.

The cryptic Tn antigen has alpha-N-acetyl-D-galactosamine residues as the immunodominant group, is responsible for polyagglutination of certain red cells by antibody and is also present on platelets. Abnormal exposure of the Tn antigen may result from a deficiency of specific galactosyl transferase activity (T-transferase) and is often associated with thrombocytopenia.

The T (Thomsen-Friedenreich) antigen is a similarly cryptic beta-D-galactosyl residue which can be exposed by treatment with neuraminidase.

Class I antigens of the major histocompatibility complex are also though to be absorbed to the surface of the platelet. In fact, platelets carry approximately 73% of the total HLA-A and -B content of the blood. Studies have clearly shown that these antigens are the most immunogenic of the various antigens expressed on the platelet surface. At the same time, it is well recognized that there can be differing expression of HLA antigens not only on different cell types but also in quantitative expression on platelets from the same individual.

The existence of distinct platelet-specific antigens was first recognized more than 30 years ago. Seven antigenic systems containing eleven different antigens have now been described, all being products of autosomal dominant genes. The PL$^A$ (Zw), PL$^E$, and KO systems are diallelic, while BAK$^a$, LEK$^a$, and DUZO have only single alleles detected thus far.

The above antigens are really epitopes on defined membrane glycoproteins (GP), which in turn possess receptor characteristics for specific platelet biochemical functions. These biochemical functions include binding of thrombin by GPIb, fibrinogen by the GPIIb/IIIa complex, and serving as the thrombin substrate by GPV.

Alloimmunization to platelets can be demonstrated using a variety of in vitro laboratory methods, including radiometric tracers, immunofluoressence, antiglobulin or complement consumption, platelet activation, and enzyme-linked immunoassays. The development of such assays has been pursued with a variety of successes, especially as relates to a crossmatching procedure.

Complement activation assays are attractive procedures in theory. In practice, however, these have poor sensitivity. Since antibody-coated platelets are removed from the circulation by macrophages, platelet adherence and phagocytosis are plausible alternatives to complement fixation tests, but the procedures so far designed are cumbersome and poorly reproducible. Although the methods utilizing the antiglobulin principle are relatively simple, sensitive, and quantitative, they all share an intrinsic complicating problem. Due to the platelet's ability to adsorb plasma components, including IgG (Triplett (1978) in Platelet Function: Laboratory Evaluation and Clinical Applications (D. Triplett, ed.) pp. 1–34, ASCP Press, Chicago), most of these assays have high background values obtained by measuring both the immune-bound and nonspecifically-bound IgG. These high background values make suspect measurements of platelet-associated IgG (PAIgG) other than those substantially above normal values, the range of which has been reported to be from 1.7 fg to 15.5 ng IgG ($7 \times 10^3$ to $1.6 \times 10^7$ molecules IgG) per platelet (Dixon et al. (1975) N. Engl. J. Med., 292: 230–236; Nel et al. (1980) Br. J. Haematol., 44: 281–290; Yesus et al. (1984) Amer. J. Clin. Pathol., 81: 1). LoBuglio et al. have introduced an $^{125}$I-labelled anti-IgG technique to lower these values to about 169±79 IgG molecules per platelet (LoBuglio et al. (1983) N. Engl. J. Med., 309: 459–463).

An object of this invention is the development of an effective in vitro platelet antibody detection assay or crossmatching procedure to identify compatible platelet donors, particularly for multitransfused patients refractory to platelet transfusion. Such a procedure preferably involves preparation of a bank of stored donor platelet samples against which a patient's serum may be screened for the present and quantity of antibody. Methods designed to store such platelet aliquots for long term use in laboratory assays have been reported. Kikler et al. took segments from pheresis bags to isolate donor platelets and use in a radiolabeled antiglobulin test (Kikler et al. (1983) Blood, 61: 238–242). However, since pheresed platelets can be stored no longer than 120 hours, the test is limited to donors accruing within such a time period. Forster et al. isolated platelets from EDTA-anticoagulated blood samples and fixed them with 1% paraformaldehyde prior to their use in a microELISA assay (Forster et al. (1983) Klin. Wochenscher, 61: 165–167). In contrast, platelets preserved either by desiccation (stored for up to thirty days) or in normal saline containing 0.01% sodium azide (stored for up to 417 days) gave reproducible results that correlated well with results obtained using fresh platelets.

Therefore, an important aspect of the present invention is the preparation of suitable donor-specific platelet "reagents" that are stable over long periods of storage, are compatible with a reliable and efficient assay, and result in minimal non-specific reactivity. Such platelet reagents may, as described in the present invention, be prepared by certain detergent solubilization of the platelet membranes, followed by the coupling of solubilized membrane components to an inert matrix for immunoassay. It is paramount, however, that the native biological activities of such solubilized components be preserved and that the detergent not interfere with subsequent biochemical or immunological assays.

Non-ionic detergents vary in their effectiveness to solubilize biological membranes and to maintain native activities of the components. The inability of these detergents to be completely removed from the reaction media because of their low critical micell concentrations, large micell sizes, and high affinity for membrane proteins limits their applicability to various test systems (Helenius et al. (1979) in Methods in Enzymology (S. Fleischer and L. Packer, eds.) Vol. LVI, p. 734–749. Academic Press, London and New York).

Both platelet-specific glycoproteins (GP) and HLA antigens have been solubilized with a variety of non-ionic detergents in efforts to study the specific roles of membrane glycoproteins in platelet immune function. Kunicki et al. localized the Pl$^{Al}$ alloantigen to the GPIIIa component using Nonidet P40 (Kunicki et al. (1979) Mol. Immunol., 16: 353–360). Triton X-100 has been widely used to characterize the structure and composition of platelet surface components (Dutcher et al. (1981) Blood, 57: 395–398), to detect monoclonal antibodies (moAb) to platelet membrane proteins (Newman et al. (1982) J. Cell Biol., 90: 249–253), and to study platelet-associated IgG in alloimmunized patients (Yohannes et al. (1983), Amer. J. Clin. Pathol., 81:81–84). Triton X-114 (Newman et al. (1982) Thromb Res., 27: 221–224) has been applied for the selective extraction of integral membrane proteins, whereas both Brijj-99 (Springer et al. (1976) Proc. Natl. Acad. Sci. USA, 73: 2481–2485) and Nonidet P40 (Parm (1979) J. Biol. Chem., 254: 8709–8712; Cook et al. (1985) Hum. Immunol., 14: 234–244) have been used to probe the structure of HLA antigens on the platelet surface.

The research of Baron and Thompson (Baron et al. (1975) Biochem. Biophys. Acta., 382–276-285) led to the introduction of the non-ionic alkyl-beta-D-glucoside detergents which have since been found to surpass cationic, zwitterionic and other non-ionic detergents in their abilities to solubilize, retain native functions of the components, and be completely removed from the lysate (Stubbs et al. (1976) Biochem. Biophys. Acta, 426–46–56; Lin et al. (1979) Biochem. Biophys. Acta, 557: 179–187; Rosevear et al. (1980) Biochem., 19: 4108–4115). Hildreth compared the capacity of several of these alkyl glucosides for solubilizing transformed cell lines, and found them as effective as or superior to other commonly used detergents in releasing antigenically active class I histocompatibility antigens (Hildreth (1982) Biochem. J., 207: 363–366).

Further, it has been shown that the immunoreactivity of solubilized membranes can be preserved following their chemical coupling to a variety of solid matrices, including cyanogen bromide-activated filter paper discs, nitrocellulose paper and polystyrene microtiter plates.

As stated above, most platelet antibody assays currently being used are designed to detect PAIgG with a marker-labeled anti-IgG, making it impossible to differentiate immune from nonimmune immunoglobulin attached to the platelet surface. In the past, investigators have attempted to block or dissociate the non-specifically bound IgG with various detergents, albumin solutions or platelet pretreatments. It is apparent, however, that these standardly used blocking methods do not altogether inhibit nonimmunospecific IgG binding to the platelet surface. This may indicate that the affinity of at least some of the nonimmune IgG for the platelet membrane is greater than the affinity described for general non-specific protein-protein binding. This phenomenon of nonimmunospecific but strong binding may be the result of receptor-like proteins for IgG on the surface of the platelet.

Cheng et al. affinity isolated and characterized a specific platelet membrane glycoprotein which interacted the $F_c$-fragment of IgG (Cheng et al. (1979) J. Biol. Chem., 254: 2165–2167). Beardsley et al. reported the binding of non-specific IgG to a 200 kilodalton glycoprotein separated by SDS-PAGE from detergent solubilized platelets (Beardsley et al. (1984) J. Clin. Invest., 74: 1701–1707). It is generally accepted that there is an isoluble platelet membrane component with a high affinity for normal, nonimmune IgG.

The present invention details a method by which random donor platelets were solubilized with the non-ionic detergent decanoyl-N-methylglucamide (Mega 10), dialyzed to remove excess detergent, and partially purified using affinity chromatography with agarose-bound IgG. The detergent lysate was immobilized onto nitrocellulose discs which were then incorporated into an enzyme-linked immunoassay to detect the presence of immunologically active platelet membrane components and clinically significant antibodies in the sera of multitransfused platelet recipients.

BRIEF DESCRIPTION OF THE DRAWINGS

FIG. 2 shows the detection and stability of nitrocellulose-bound PLy. Nitrocellulose discs were dotted with 20 ug of PLy as described herein, and were then incubated with 1:10 dilutions of: (NS) normal sera, (Pl$^{A1}$) anti-Pl$^{A1}$, (AF) alloimmune serum, (A1) anti-HLA-A1 or (B8) anti-HLA-B8, or 500 ng of monoclonal antibody to the platelet glycoproteins GPIb, GPIIb, or GPIIb/IIIa. A 1% bovine serum albumin solution (BSA) was used as a control. All dilutions were made in 10 mM-TBS, pH 7.4. Bound antibody was detected with alkaline phosphatase-conjugated anti-IgG using freshly prepared discs (open bars) and discs stored for 100 days (hatched bars).

FIG. 3 shows detection and stability of nitrocellulose-bound PAb. Nitrocellulose discs were dotted with 20 ug of PAb as described herein, and were then incubated with 1:10 dilutions of: (NS) normal sera, (P1$^{41}$) anti-P1$^{41}$, (AF) alloimmune serum, (A1) anti-HLA-A1 or (B8) anti-HLA-B8, or 500 ng of monoclonal antibody to the platelet glycoproteins GPIb, GPIIb, or GPIIb/IIIa. A 1% bovine serum albumin solution (BSA) was used as a control. All dilutions were made in 10 mM-TBS, pH 7.4. Bound antibody was detected with alkaline phosphatase-conjugated anti-IgG using freshly prepared discs (open bars) and discs stored for 100 days (hatched bars).

SUMMARY OF THE INVENTION

Figure 1:
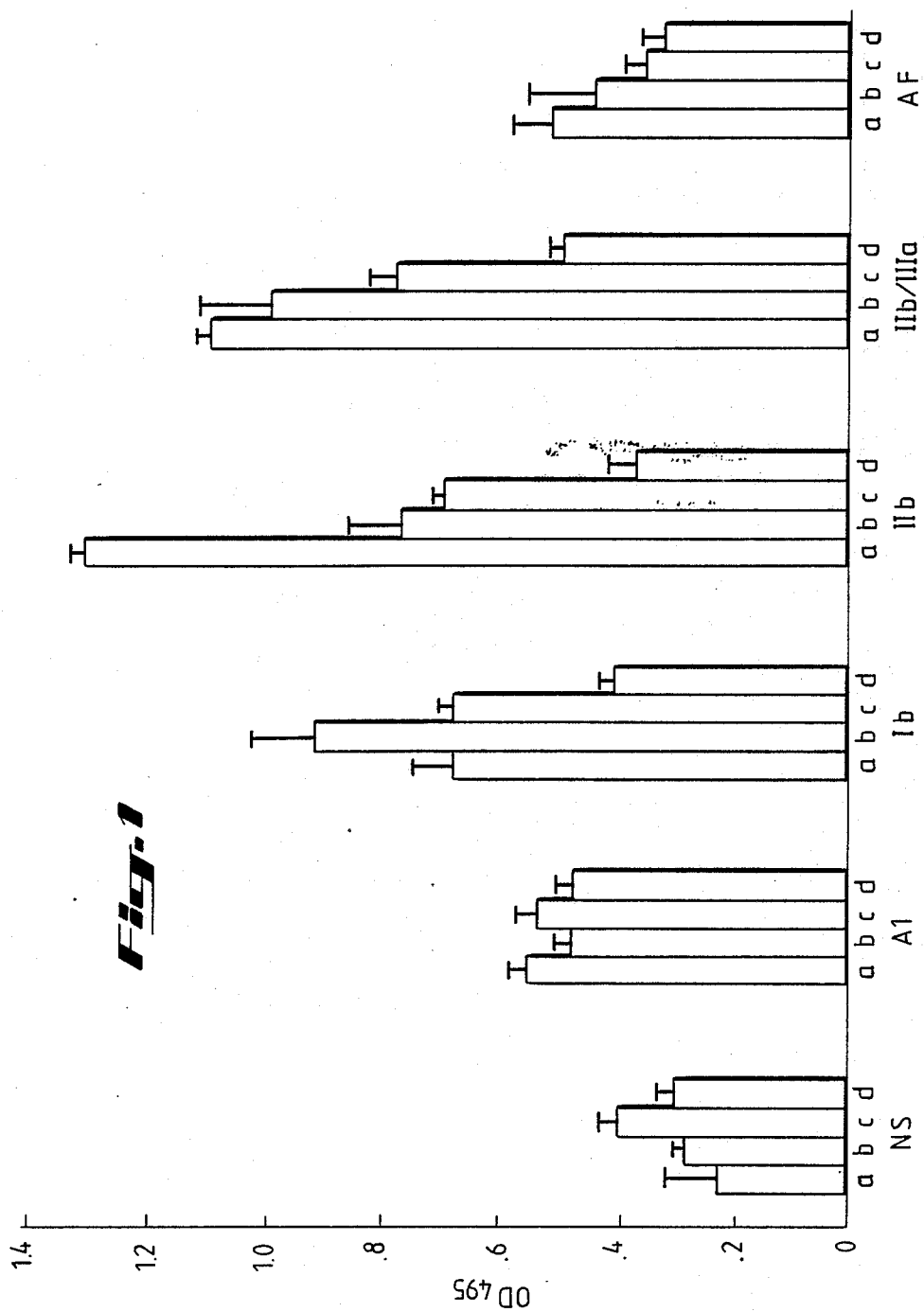
FIG. 1. shows the ability of antibody to detect various quantities of nitrocellulose-bound platelet detergent lysate. Platelet detergent lysate (PLy) was prepared as described herein and (a) 20 ug, (b) 10 ug, (c) 5 ug, or (d) 1.0 ug was applied to nitrocellulose discs. Normal serum (NS), anti-HLA-A1 (A1), or alloimmune serum (AF), diluted 1:10 in TBS, or 500 ng of moAb to GPIb, GpIIb, or GPIIb/IIIa were incubated with the discs, and bound antibody was subsequently detected with alkaline phosphatase-coupled anti-IgG.

The present invention involves a method for producing a substrate useful in a system for the detection of antibodies directed against platelet antigens. This method comprises several steps. A platelet sample of interest is initially treated with an aqueous solution comprising a dialyzable nonionic detergent. This initial treatment is under conditions to solubilize platelet components and produce a platelet lysate. For an assay to detect the presence of antibody to platelets, the "platelet sample" would be absorbed supernatant prepared from a pool of aliquots from 30-40 units of platelet-rich plasma. For a crossmatch assay, "platelet sample" would be absorbed supernatant prepared from an individual unit of pheresed platelets. Such conditions may involve treatment of a platelet sample with an aqueous solution comprising nonionic detergent at a concentration between about 0.2% and about 0.5%. Platelet antigens are most preferably solubilized for about 30 min and at about 0° C. in an aqueous solution comprising about 1 mg dialyzable nonionic detergent per mg platelet protein.

Insoluble particles and excess detergent are preferably next separated from the lysate to produce a solution comprising solubilized platelet antigens. Insoluble particles are preferably removed by centrifugation of the lysate and detergent is preferably removed by dialysis.

Substances nonimmunospecifically binding to human IgG are then removed from said solution to produce partially purified platelet antigens. The removal of these substances nonimmunospecifically binding to human IgG preferably involves contacting the solution with human IgG attached to a solid matrix. For example, the platelet lysate, freed of insoluble particles and excess detergent may be chromatographically run through a column of IgG-agarose.

The partially purified platelet antigens resulting from these manipulations are then preferably affixed to a solid matrix. The solid matrix preferably comprises nitrocellulose paper, polystyrene or latex but may be any solid matrix suitable for the abstraction from a biological sample and/or assay of antibodies binding to the affixed purified platelet antigens.

Insofar as the present invention concerns a method for detecting antibodies directed against platelets in a biological sample, the method comprises, in addition to the preparation of the substrate described above, the steps of contacting said solid matrix with a solution comprising the biological sample and measuring the amount of antibody bound to the solid matrix.

When the biological sample of interest is a platelet source and the identification of a platelet source immunologically compatible with a prospective platelet recipient is an object of the present invention, the method, in addition to producing a substrate as described above with the platelet sample being from the platelet source, involves additional steps. As a negative control, a sample is obtained from a pool of previously untransfused male individuals having an AB positive blood type. Such previously untransfused males should not have antibodies against platelet antigens. An antibody-containing sample is obtained from a prospective platelet recipient, in need or potentially in need of platelet transfusion.

A first portion of said affixed partially purified platelet antigens (substrate) is contacted with an antibody-containing sample from the prospective platelet recipient under conditions facilitating binding of antibody specific for platelet antigens to the affixed partially purified platelet antigens. A second portion of said affixed partially purified platelet antigens is contacted with an antibody-containing sample from the previously untransfused male having an AB positive blood type under the same conditions. A first level of antibody bound to the first portion of the affixed partially purified platelet antigen and a second level of antibody bound to the second portion of the affixed partially purified platelet antigens are then determined. This determination may be by any of numerous means known to those skilled in the relevant arts and include Enzyme Linked Immunoadsorbent Assays (ELISA) and determinations of turbidity, particularly in the latter case where the solid matrix is latex in bead form.

The first level of bound antibody is then compared to the second level of bound antibody. A platelet source immunologically compatible (not having substantial levels of antibodies directed against platelet antigens of the platelet source) with said prospective platelet recipient is identified when said first level is not substantially greater than said second level. The processes of the present invention are particularly useful to cross-match immunologically compatible platelet sources with patients previously refractory to circulating platelet increases after platelet transfusion.

Preferred detergents for use in the practice of the present invention are alkyl-N-methylglucamides or alkylglycosides, more preferably the former. Among the more preferable alkyl-N-methylglucamides are decanoyl-N-methylglucamide, nonanoyl-N-methylglucamide, octanoyl-N-methylglucamide and heptanoyl-N-methylglucamide. The most preferred detergent of the present invention is decanoyl-N-methylglucamide. Usable alkylglycosides include n-decyl beta-D-glucopyranoside, n-dodecyl beta-D-glucopyranoside, n-dodecyl beta-D-maltoside, n-heptyl beta-D-glucopyranoside, n-hexyl beta-D-glucopyranoside, n-octyl beta-D-glucopyranoside, n-nonyl beta-D-glucopyranoside and n-octyl-alpha-D-glucopyranoside.

DESCRIPTION OF THE PREFERRED EMBODIMENT

These specifics are presented to illustrate preferred embodiments and utilities of the present invention and are not meant to limit the present invention unless otherwise specifically stated in the claims appended hereto.

The following reagents were purchased from Sigma Chemical Co., St. Louis, MO: Decanoyl-N-methyl-glucamide (Mega-10); Polyvinylpyrolidone; gamma globulin-free bovine serum albumin (BSA); Pooled human male AB serum; poly-L-Lysine; Agarose-bound human IgG; 3-amino-9-ethylcarbazole; Alkaline phosphatase conjugated F(ab')2 fragments of sheep anti-mouse IgG and goat anti-human IgG; p-nitrophenyl-phosphate substrate and diethanolamine. Bio-Rad dye-reagent protein assay was obtained from BioRad Laboratories, Richmond, CA. Nitrocellulose paper (0.45 um) was purchased from Schleicher and Schuell, Inc., Keene, NH. Avidin-Biotin test reagents were supplied by Vectastain Labs, Inc., Burlingame, CA. Tissue typing trays were purchased from One Lambda, Los Angeles, CA, and Geometric Data, Wayne, PA. Anti-P1[41] alloantiserum was a gift from Dr. R. Aster (Blood Center of Southeast Wisconsin, Milwaukee, WI). Mouse monoclonal antibodies (moAb) from ascites fluid were generously provided by Dr. R. P. McEver (University of Texas Health Science Center, San Antonio, TX). Sera from alloimmunized individuals (AF, DP) were collected from the U.T.M.D. Anderson Hospital Blood Bank. All other chemical were of analytical grade.

Platelet-rich plasma was prepared by differential centrifugation of Group O, Rh-positive blood anticoagulated with citrate phosphate dextrose adenine. Platelets were isolated according to the procedure described by Schiffer and Young (1983). Purity was assessed by light microscopy and the preparation shown to contain less than one red blood cell or leukocyte per 1000 platelets. Platelet counts were electronically performed using the Coulter S-Plus. Mononuclear cells were isolated using Ficoll-Hypaque density gradients as described by Boyum (1968).

Platelet preparations were centrifuged, the supernates discarded, and the platelet buttons weighed. A 10% stock solution of detergent was made in methanol, and diluted with 50 mM-Tris-HCl, pH 8.0, containing 0.15M-NaCl (TBS) and 1 mM-phenylmethanesulfonyl fluoride to make a 0.5% working solution. The platelets were solubilized using a detergent/protein ratio of 1:12 for 30 min on ice with occasional shaking. This lysate (PLy) was centrifuged at 50,000×G for 1 hr at 4° C., and the supernate dialyzed overnight at 4° C. against 10 mM-TBS, pH 8.0, 0.02% sodium azide. Protein concentrations were determined colorimetrically. Bovine serum albumin was used as the standard. Aliquots of PLy were frozen at −70° C.

Five hundred microliters of agarose-bound IgG (AgIgG) were centrifuged for 2 min at 3000×g and the supernate removed. Ply was diluted to 1.5 mg/ml with TBS and 1.0 ml of this was added to the AgIgG and placed on a rotating platform for 30 min at RT. The mixture was centrifuged as above, the supernate removed, and added to 500 ul of packed, fresh AgIgG. The incubation was repeated and the absorbed supernate (PAb) removed after centrifugation. Protein determinations were made of the supernates following each absorption. Aliquots of PAb were stored at −70° C.

Bovine serum albumin (BSA), 1.0 mg/ml in TBS, was absorbed using the above conditions to determine the specificity of protein adherence to AgIgG.

Nitrocellulose discs (NC) were prepared using a standard 6-mm hole punch. Before use, the discs were hydrated with distilled water for 5 min and then air dried. PLy/PAb of various concentrations in volumes of 10–15 ul were dotted onto NC and allowed to air dry. NC discs were stored in airtight containers at 4° C. until use. All subsequent steps were performed at room temperature unless otherwise stated.

For the ELISA, one NC was placed in a 12×75 mm glass tube and 100 ul (microliter) of 1% polyvinyl-pyrolidone-1% bovine serum albumin solution were added to block excess binding sites. After 30 min incubation, the blocking solution was aspirated and 100 ul of normal control serum, 1% BSA, or the appropriate test serum (diluted in 10 mM-TBS, pH 7.5, 1 mM CaCl$_2$) were added to duplicate tubes. The discs were incubated in a 37° C. water bath for 1 hr, followed by three-10 min washes with 10 mM-TBS, 0.01% goat serum. Two hundred microliters of the enzyme-conjugated anti-IgG (diluted 1:750 in TBS) were added, and the reaction mixture was incubated for 1 hr with continuous shaking. The enzyme conjugate was aspirated and the discs were washed three times with TBS. Alkaline phosphatase activity was detected at 37° C. following the addition of 200 ul p-nitrophenylphosphate substrate, 1.0 mg/ml in diethanolamine buffer, pH 9.8, according to Schiffer and Young (Schiffer et al. (1983) Blood, 61: 311–317). Optical density readings at 405 nm were made using a Dynatech micro-ELISA reader.

One microliter of PLy (1.0 mg/ml in 10 mM-TBS) was added to each well of a commerically prepared, 60-well microtiter tray containing 1.0 ul of HLA-A,B, or C locus-specific antiserum, and the contents were incubated for 30 min at room temperature. Autologous or random lymphocytes, isolated as described above, were added to each well and the procedure for a standard microcytotoxicity assay followed (Mittal et al. (1968) Transplantation, 6: 913–916).

Platelets were isolated and pooled from the pilot segments of 40 platelet rich plasma units. An aliquot of this pool was bound to glass sides with poly-L-lysine using a modified method of Trinidad et al. (Trinidad et al. (1983) in Abstracts and the Ninth Annual Meeting of the Amer. Assoc. Clin. Histocompatibility Testing, Chicago, Il., p. 50). All steps were performed at room temperature. Ten microliters of antiserum (diluted 1:!10 with TBS) which had been previously absorbed for 30 min with either 5 ul PLy (1.0 mg/ml) or with TBS were added to the bound platelets. After washing with TBS, 10 ul of biotinylated anti-IgG were added for 30 min. The slides were washed and 10 ul of an avidin-biotinylated lactoperoxidase solution were added for 45 min. Enzyme activity was detected microscopically after a 5 min incubation with 3-amino-9-ethylcarbazole (0.5 mM in 100 mM-sodium acetate buffer, pH 5.2).

Solubilization of 1.0 g (approximately 2.3×10$^{10}$) platelets typically yielded 26.0±3 mg protein. The same yield was obtained when the detergent/protein ratio was decreased twofold. Some insoluble material was seen after ultracentrifugation, and none was observed following dialysis. Thawing and centrifugation of frozen aliquots never reduced the protein concentration of any extract tested.

Table 1 details the results of multiple absorption of two different PLy preparations and the BSA control solution. A consistent loss of protein was noted with two absorptions of the PLy with AgIgG. A third treatment with fresh AgIgG, however, did not further decrease the protein concentration. The total loss of protein with this procedure for the two Ply preparations was 32% and 25%. All subsequent absorptions of PLy were therefore carried out at the ratio of 1.5 mg PLy/1.0 ml of AgIgG. The average loss of protein using eight different PLy preparations was 29.4±4%. This absorption was a specific phenomenon, as demonstrated by the recovery (107%) of BSA following identical treatment with AgIgG.

TABLE 1

Recovery of Protein Following Absorption of Platelet Lysate with Agarose-IgG

| Exp. | mg PLy added to agarose-IgG | mg (%)* PAb recovered following absorbtion | | |
|---|---|---|---|---|
| | | #1 | #2 | #3 |
| I | 1.50 | 1.16 (78) | 1.03 (69) | 1.02 (68) |
| II | 1.50 | 1.26 (84) | 1.10 (73) | 1.13 (75) |
| BSA | 1.00 | 1.07 (107) | | |

*percent of starting material

The ability of PLy to inhibit specific, complement-mediated lymphocytotoxic antibody is shown in Table 2.

TABLE 2

Inhibition of Antibody-mediated Class I Lymphocytotoxicity With PLy and PAb.

| DONOR | HLA LOCUS | ANTIGEN PRESENTED ON DONOR'S LYMPHOCYTES | INHIBITION BY DONOR'S PLy/PAb* |
|---|---|---|---|
| I | A | 11 | + |
| | | 9 | + |
| | | 24 | + |
| | B | 40 | + |
| | | 5 | + |
| | | 51 | + |
| II | A | 3 | N |
| | | 29 | + |
| | B | 18 | + |
| | | 12 | + |
| | | 45 | + |
| III | A | 9 | + |
| | | 24 | + |
| | B | 5 | +* |
| | | 51 | + |
| | | 12 | N |
| | | 44 | N |

*+ = >95% inhibition
N = <5% inhibition

Except in the cases of anti-A3 (donor II) and anti-B44(12) (donor III), detergent extracts of donors' platelets completely inhibited cytotoxicity of antisera directed against HLA antigens on autologous lymphocytes and against identical antigens on allogenic lymphocytes. PLY never inhibited the cytotoxic reactions of antiserum directed against non-self antigens, although a slight decrease (<20%) in reactivity of antisera to known crossreactive antigens was occasionally noted. It is important to note that whole platelets from Donor 2 inhibited cytotoxic activity of all specific antisera except anti-HLA-A when tested in the same assay.

PLy and PAb had the capacity to completely absorb anti-Pl$^{41}$ activity as measured by using a sensitive avidin-biotin immunoperoxidase assay. Anti-Pl$^{41}$ absorbed with the PLy or PAb failed to result in any which was bound immunoperoxidase activity. The same lack of peroxidase activity was obtained when serum collected from an individual alloimmunized to platelets as a result of multiple transfusions or when HLA-specific alloantiserum was absorbed.

There was a complete loss of enzyme activity following its absorption with PLy. However, little reduction in the intensity or pattern of staining of the platelets was noted when compared to the control. This was because PAb had that membrane component(s) responsible for the binding of nonimmune IgG previously absorbed with the agarose-bound Ig.

In order to determine the optimal amount of solubilized material to bind to the NC discs for the ELISA, decreasing quantities of PLy were applied to the discs and incubated with normal serum or antibody to the various antigens shown in FIG. 1. The major platelet glycoproteins GPIa, GPIb, GPIIb/IIIa complex, HLA-A1, and the allodeterminate(s) defned by serum AF were all detectable with as little as 1.0 ug of PLy per NC disc. With this quantity of PLy, however, it was not possible to discriminate between the normal serum control and AF, the latter showing oilly a 6% increase in average reactivity. Since 20 ug/disc gave the highest reactivity in general, this amount was used in all subsequent experiments.

The effect of absorption of PLy with AgIgG on the binding of normal serum in shown in Table 3.

TABLE 3

Effect of Absorbtion of PLy with Agarose-IgG on the Binding of Normal Serum.

| Sample | Avg. OD$_{495}$ (± s.d.) | | % Decrease |
|---|---|---|---|
| | PLy | PAb | |
| NS-1 | .22 (.02) | .03 (.02) | 87 |
| NS-2 | .25 (.03) | .09 (.02) | 64 |
| NS-3 | .29 (.01) | .10 (.01) | 64 |
| NS-4 | .14 (.02) | .03 (.01) | 80 |
| NS-5 | .26 (.01) | .04 (.01) | 87 |
| PHS | .34 (.02) | .07 (.01) | 80 |
| average | .25 (.02) | .06 (.01) | 77 (11) | values have been corrected for enzyme substrate binding to discs, OD$_{495}$ = .20 ± .02

Sera from five individuals, as well as from a commercially obtained pool of human serum were incubated with discs dotted with either PLy or PAb, and probed with enzyme conjugated anti-human IgG. The level of non-specific binding of the secondary reagents to the nitrocellulose was determined by substituting TBS for the primary antibody. An average 77% (range: 63-90) decrease in detectable IgG was noted in the PAb values compared to PLy. Secondary reagent binding contributed 0.20±0.2 optical density (OD) units to each reaction, and was therefore subtracted from all subsequent readings.

The ELISA was performed using both freshly prepared discs and those stored at 4° C. This was done to establish the stability of NC-bound PLy. Using PLy discs, no loss after a 100 day storage period of HLA-A1, -B8, PL$^{A1}$, or GPIb activity was seen. A storage-dependent decrease of about 35% and 15% was evident in the GPIIb and GPIIb/IIIa reactivity, respectively (FIG. 2). These latter values were still, however, a 2.5-fold greater than the normal serum control, and almost five-fold higher than the BSA control.

The same antigens were as equally stable in the NC-bound PAb following a 100 day storage period (FIG. 3), although an 18% and 15% decrease in the HLA-A1 and -B8 activity, respectively, was noted. These values were still significantly above the normal serum controls.

The sensitivity of this ELISA system was also investigated by incubating decreasing quantities of antibody with a consistent amount of immobilized Ply/PAb (20 ug/disc). As seen in Table 4 using PLy-bound discs, specific antibody can be detected even at a dilution of 1:100, with OD values 1.7 and 1.5-times higher than the normal serum control for anti-PLA1 and serum AF, respectively.

TABLE 4

Ability of Nitrocellulose-bound PLy and PAb to Detect Decreasing Quantities of Alloantibody.

| Sample | Dilution$^{-1}$ | Avg. OD$_{495}$ ($\pm$s.d.)* | |
|---|---|---|---|
| | | PLy | PAb |
| NS | 10 | .22 (.04) | .02 (.01) |
| | 50 | .40 (.06) | .17 (.01) |
| | 100 | .38 (.07) | .10 (.03) |
| PL$^{A1}$ | 10 | .45 (.01) | .40 (.01) |
| | 50 | .64 (.04) | .59 (.02) |
| | 100 | .62 (.02) | .40 (.02) |
| HLA-A1 | 10 | .62 (.01) | .75 (.02) |
| | 50 | .46 (.07) | .43 (.05) |
| | 100 | .31 (.01) | .43 (.01) |
| AF | 10 | .53 (.03) | .27 (.02) |
| | 50 | .65 (.06) | .47 (.03) |
| | 100 | .58 (.05) | .45 (.06) |

*values have been corrected for substrate binding to discs, OD$_{495}$ = .20 $\pm$ .02.

The anti-HLA-A1, however, failed to show an increase over the control at both 1:50 and 1:100 dilutions. Two- to three-fold increases were seen for all three antisera at 1:10.

These results may be contrasted with those obtained with the same assay using NC-bound PAb, also shown in Table 4. While enzyme activities were four-fold higher than PLy values in all antisera at a 1:100 dilution, most noticeable were the values obtained at 1:10 dilutions. These were 20 to 35 times higher than the control serum values. Normal serum binding at a 1:10 dilution was greatly reduced following absorption of the PLy, to one-tenth (0.02) the value observed with PLy-bound discs (0.22).

The values in Table 5 demonstrate the sensitivity of the assay when tested against decreasing amounts of monoclonal antibody (moAb).

TABLE 5

Ability of Nitrocellulose-bound PLy and PAb to Detect Decreasing Quantities of Monoclonal Antibody.

| moAb | ng Added | Avg. OD$_{495}$ ($\pm$s.d.)* | |
|---|---|---|---|
| | | PLy | PAb |
| GPIIb/IIIa | 500 | 1.40 (.02) | 1.02 (.01) |
| | 200 | 1.05 (.02) | 1.11 (.05) |
| | 100 | .78 (.08) | .88 (.03) |
| | 50 | .40 (.02) | .36 (.05) |
| | 20 | .35 (.01) | .40 (.01) |
| GP Ia | 20 | .45 (.02) | .41 (.01) |
| GP IIb | 20 | .33 (.02) | .38 (.01) |

*BSA control = .22 $\pm$ .05
Anti-mouse IgG = .16 $\pm$ .01

Compared to the BSA or anti-mouse IgG control values of 0.220 and 0.160, respectively, as little as 20 ng of monoclonal antibody (moAb) directed against GPIb, GPIIb, or GPIIb/IIIa could easily be detected. Optical density values of these moAb at this concentration were at least 30% greater than the controls, while 500 ng of the GPIIb/IIIa antibody were 5-7 times higher. Compared to PLy, less than an 8% loss in activity of any of the moAb was noted using the PAb discs, showing that these immunologically important surface antigens have not been lost during the absorption.

The ELISA system was tested for its ability to detect platelet antibody in the serum of two thrombocytopenic patients, alloimmunized through multiple platelet transfusions (sera AF and DP). These sera were strongly positive in a the platelet antibody screen routinely performed by the Histocompatibility Test Laboratory at M.D.A.H., both being reactive at a serum dilution greater than 1:90, as well as being cytotoxic to more than 60% of a 56-cell panel of cells in a lymphocytotoxic antibody screen.

Figure 4:
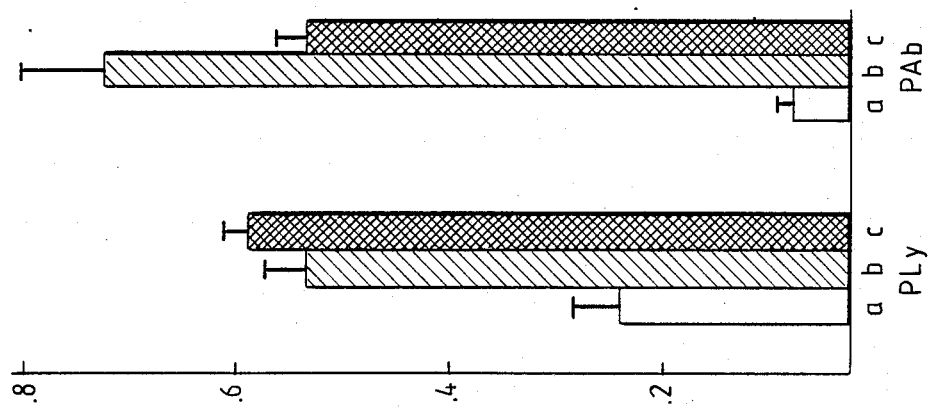
FIG. 4 shows the ability of nitrocellulose-bound PLy and PAb to detect alloantibodies in immunized patients. Nitrocellulose-bound PLy or PAb, 20 ug/ml, were prepared as described herein, and each incubated with 100 ul of (a) normal serum, (b) AF or (c) DP, diluted 1:10 in TBS. Alkaline phosphatase-coupled anti-IgG was used to detect the bound antibody.

In FIG. 4, this strong reactivity of AF and DP with immobilized PLy was reflected by a 2.3 to 2.5-fold increase in enzyme activity above the control, respectively. However, when the same sera was used with the NC-bound PAb, AF reactivity increased to ten times the values obtained with PLy, and 23.7 times greater than the control values. Likewise, DP reactivity with PAb was shown to be 16.7 times higher than the control. The increase in reactivity of AF from 0.54 from PLy to 0.71 with PAb probably represented an increased amount of specific proteins bound to the discs following absorption of PLy with AgIgG.

Figure 5:
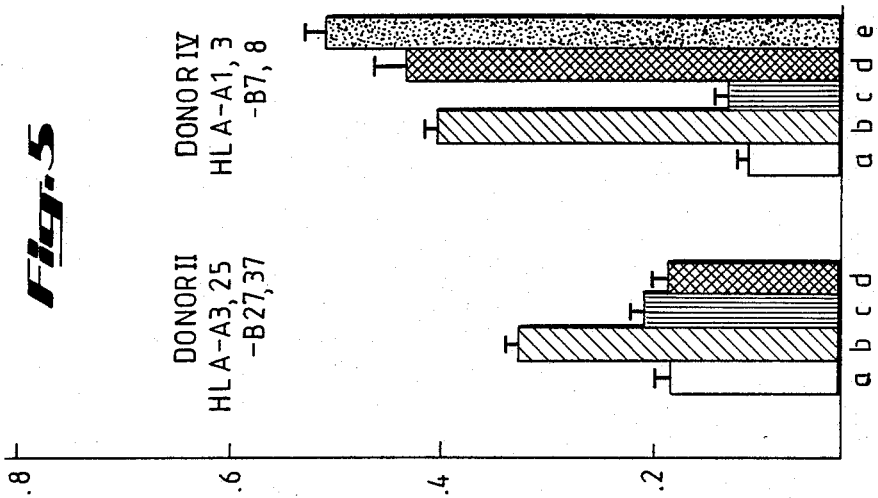
FIG. 5 shows the retention of activity of class I histocompatibility antigens in PAb. Platelet detergent lysates were prepared from two HLA-typed individuals, absorbed with AgIgG and applied to nitrocellulose discs (20 ug/disc) as described herein. Normal serum (a), antiserum to P1$^{41}$ (b), anti-HLA-A3 (c), anti-HLA-BB (d), and anti-HLA-A1 (e), all diluted 1:10 with TBS, were used to probe for the retention of activity of these antigens in an alkiline phosphatase-coupled anti-IgG immunoassay.

The ELISA results of two different PAb using alloantisera to measure the presence of HLA-specific antigens are presented in FIG. 5. Although donor II presents HLA-A3 on his lymphocytes (see Table 2), its expression in PAb is minimal, showing a 5.3% increase in reactivity when compared to the normal serum control. As expected, no HLA-B8 could be detected. Donor IV (HLA-A1,3; B7,8) reacted strongly with antisera to both A1 and B8 with increases in reactivity of 170% and 146%, respectively, but demonstrated only a 6% increase in anti-A3 reactivity above the control.

Various quantitative assays for the measurement of platelet-associated immunoglobulin (Ig) have been developed to aid in the study of the pathophysiology of immune mediated platelet destruction. An inherent difficulty to most of these, however, has been the fact that both specific and non-specific antibody binding are indistinguishable. In fact, the contribution of the latter to the total detectable antibody is high enough to often render these test results useless. This is especially problematic since the difference between Ig concentrations on normal and antibody-sensitized platelets can be quite small. The present invention includes a method that overcomes some of these problems. A benefit of use of the present invention is an in vitro crossmatch assay that could be used to predict the outcome of platelet transfusions.

The present invention involves the use of a dialyzable nonionic detergent such as an alkyl-N-methylglucamide or alkylglycoside to solubilize human platelets for functional studies of the membrane components. Of important in the method of the present invention is the ability to remove excess detergent through dialysis, thereby obviating problems such as those involving reconstitution and protein concentration measurements. In addition, it is known that detergent can prevent the binding of antigen by moAB and can inhibit assays that involve immunoprecipitation of antigens from detergent solutions. It has previously been shown that the plastic microwells used for some ELISA and hybridoma screening procedures are inefficient at binding protein in the presence of detergent. Although other methods have been used to remove detergents from membrane lysates, none was as simple and without as many deleterious effects on the solubilized membrane components as dialysis.

The most preferred detergent of the present invention is decanoyl-N-methyl glucamide (Mega-10). Platelets were solubilized by Mega-10 as described above, with an efficiency of about 27%, based on the dry weight of approximately $10^6$ platelets of 4 ug. This is comparable to the data presented by Kunicki et al. using 0.5% NP40 solubilized, radiolabeled platelets. Twenty micrograms of material bound to each disc, then, represents the lysate from about $1.8 \times 10^7$ platelets, which should allow for the detection of even minor components of the platelet membrane in a crude preparation of low levels of specific antibody.

One of the primary objectives of the present invention is to eliminate or reduce to an insigificant level the binding of nonimmune IgG to the platelet surface components. Previous attempts by the inventor to inhibit this "non-specific" or nonimmunospecific binding involving various standard blocking reagents including detergents, gelatin, casein, low ionic strength buffers, or with increased incubation temperatures, were unsuccessful. This led to the hypothesis that this binding was, in fact, specific although not immunospecific, with an affinity for platelet membrane component(s) strong enough to resist dissociation with the usual methods employed to reduce such IgG absorption. The results obtained following absorption of detergent solubilized platelets with agarose-bound IgG indicate that such membrane components do exist and that their removal does not alter the presence in PAb of immunologically relevant membrane antigens.

The ability of the dialyzed, Mega-10 solubilized PLy/PAb to inhibit specific, complement-mediated lymphocytotoxicity is in contrast to previous attempts by Cook et al. (Cook et al. (1985) Hum. Immunol., 14: 234-244) in which NP40 present in the preparation nonspecifically inhibited cytotoxicity, and to work by the inventor with Triton X-100, the presence of which nonspecifically bound the cells. The fact that PLy from a donor known to possess HLA A-3 (Donor II) or B-44(12) (Donor III) did not inhibit lysis of any population of lymphocytes expressing these antigens was notable. It has long been recognized that the platelets and leukocytes from the same subject may type discrepantly for some HLA antigens. Interestingly, the PLy from donor III, whose lymphocytes contained the B-44 private epitope, did not inhibit either anti-B-12 (the public epitope) or anti-B-44 activity, whereas antisera to B-12 and the B-45 subtype were completely inhibited by PLy from Donor II, whose lymphocytes express both these antigens. This lack of inhibition could be due in part to a low level or antigen expression. This might occur if, in fact, these histocompatibility antigens are absorbed onto the surface of platelets. Indeed the ELISA results reported here indicate that although a low level of HLA-A3 is detected, the quantity of this antigen, or perhaps its molecular conformation in the detergent lysate renders PLy/PAb incapable of absorbing anti-A3 activity under the conditions described and thus, cannot inhibit lymphocytotoxicity. Recent evidence supporting the former phenomenon has been presented by Saidman et al. (Saidman et al. (1986) in Abstracts of the Twelfth Annual Meeting for the Amer. Soc. of Histocompatibility and Immunogenetics, New Orleans, LA., p 91), who used fluorescent cell sorting analysis and monoclonal antibodies to various public and private HLA epitopes to demonstrate the varied level of expression of the antigens on platelets. This inhibition assay could prove useful for determining which HLA antigens are present on platelets in amounts sufficient to elicit an immune response or to be recognized by antibodies and fix complement. These results would provide valuable information for platelet transfusion therapy.

The fact that stored NC-immobilized PLy-PAb is stable over an extended period is of value to both research and clinical laboratories. As alluded to by Newman et al., because hundreds of discs can be made at one time, hybridoma or immune serum screening can be accomplished with both rapidity and reproducibility. Also, the immunological function of purified and immobilized membrane glycoproteins can be easily studied in this manner. Especially evident is the sensitivity of the assay when using small quantities of immobilized antigen or moAB.

It was fortuitous that two allosera with broadspecific antibodies could be found to test in this ELISA. Although the reactivities of both AF and DP sera are obviously greater than that of normal sera to PLy, the use of PAb in such as assay should be a benefit in exaggerating the difference between low positive and normal serum control values.

Also relevant to clinical laboratories is the fact that moAB probes can be used to detect the level of expression of specific platelet glycoproteins using PAb prepared from patients with thrombocytopenic conditions such as Bernard-Soulier syndrome (a severe reduction of GPIb expression), or Glanzman's thrombocytopenia (a decrease in the amount of membrane associated GPIIb and GPIIIa). These as well as other still unidentified antigens are implicated as targets for platelet-directed antibodies in idiopathic, disease-associated, and alloimmune thrombocytopenias. The application of this immunoassay to routine platelet crossmatching is readily envisioned.

Serum samples will be collected from patients with clinically demonstrable refractoriness to platelet transfusions. An aliquot of the platelet rich plasma will be removed from the units selected for transfusion. The platelets will be solubilized, absorbed with aqarose-bound IgG, and the PAb immobilized on the NC discs for use in the described ELISA. The predictive value of this assay as a crossmatch procedure will then be done retrospectively by monitoring the posttransfusion platelet increment and comparing it to the obtained ELISA results.

Van der Velden et al. (Van der Velden et al. (1986) Br. J. Haematol., 62-635-640) have used a seemingly adaptable "Z-score" calculation to predict the transfusion outcome based on results of a $^{51}$-Cr-platelet lysis assay. This Z-score is expressed as the difference between test values and transfused, nonrefractory controls relative to the standard deviation of the control values. In that study, a score of 3 or less was determined to be a negative crossmatch. Such a value, of course, would have to be determined by a laboratory seeking to quantitate successful transfusion predictabilities.

The determination of circulating antibodies to platelets has well documented importance as both adjunct and confirmative information for clinicians. This is attested to in the literature by the number and variety of platelet antibody assays attempted over the years. To date, however, a simple, sensitive, and rapid assay has not been developed due especially to the inherent difficulties in working with platelets in vitro. A passive latex agglutination test (LAT) would provide such an assay not only to the pathologist in the institutional medical laboratory, but also to the physician in his private clinic or office. Although many LAT for the detection of antigen (i.e. antibody bound to the latex beads) are in widespread use, few products offer immobilized heterlogous antigen preparations on the beads, the latter being biochemically a more complex problem.

In preliminary adaptations of latex agglutination techniques to a platelet antibody test, a Platelet Antibody Detection Reagent (PADR) comprising PAb prepared from pooled platelets has been bound to latex (polystyrene) beads of several sizes. The mechanism for coupling proteins to latex beads is not completely characterized, although hydrophobic interactions are implicated and all that is apparently necessary (no special chemical coupling is required to attach proteins to latex).

Using 1 micron diameter beads, (a) the maximum amount of PADR bindable to a given quantity of beads has been found to be about $1.3 \times 10^{-8}$ ug/particle and (b) a theoretical number of molecules of solubilized platelet material (based on an average molecule weight of 100 Kd of the solubilized platelet membrane components separated by polycrylamide gel electrophoresis) bound per latex bead was found to be approximately 6200 molecules/particle.

Quantitative macroscopic agglutination of these beads following addition of known positive antiserum has not yet been accomplished, however, using various antigen concentrations on the beads and dilutions of the test antisera.

Critical factors in any agglutination assay such as LAT are the antibody concentration in the serum and the amount of antigen bound to the matrix (latex beads, red blood cells, etc.). The optimum number of antigen molecules must be bound to the beads that will allow crosslinking of the particles by the antibody, resulting in visible agglutination. Very few reports have been found in the literature regarding the immobilization of antigen onto latex beads. Those that have been found offer no quantitative methodology for determining an optimum antigen-latex bead ratio.

It is believed that a minimal amount of concentrated laboratory investigation would solve this problem, and result in a valuable reagent for clinical laboratories.

The present invention comprises a procedure by which platelet crossmatching reagents can be easily prepared for use in a semiquantitative immunoassay. Long term storage of these reagents makes it possible to screen a large donor pool and select donors compatible with a patient prior to harvesting platelets from any of the selected individuals.

Changes may be made in the construction, operation and arrangement of the various parts, elements, steps and procedures described herein without departing from the concept and scope of the invention as defined in the following claims.

What is claimed is:

1. A method for producing a substrate useful in the detection of antibodies directed against platelet antigens, the method comprising the steps of:
    treating a platelet sample with an aqueous solution comprising a nonionic detergent to solubilize platelet antigens comprising HLA and platelet-specific antigens of the sample and to produce a lysate, said nonionic detergent being sufficiently separable from the lysate to minimize interference with subsequent binding of antibodies directed against platelet antigens to platelet antigens;
    separating insoluble particles and excess detergent from the lysate to produce a solution comprising solubilized platelet antigens;
    contacting said solution with matrix-bound human IgG to remove substances nonimmunospecifically binding to the matrix-bound human IgG from said solution to thereby produce partially purified platelet antigens; and
    affixing the partially purified platelet antigens to a solid matrix to produce a substrate useful in the detection of antibodies directed against platelet antigens.

2. A method for providing a substrate useful in the detection of antibodies directed against platelet antigens, the method comprising the steps of:
    solubilizing a platelet sample for about 30 min and at about 0° C. in an aqueous solution comprising about 1 mg of an alkyl-N-methylglucamide or an alkylglucoside nonionic detergent per mg platelet protein to produce solubilized platelet antigens comprising HLA and platelet-specific antigens;
    separating insoluble particles and excess detergent from the solubilized platelet antigens so as to minimize detergent interference with binding in subsequent assays of antibodies directed against the platelet antigens to platelet antigens and to produce a solution of solubilized platelet antigens;
    contacting said solution with matrix-bound human IgG to remove substances nonimmunospecifically binding to the matrix-bound human IgG from the solution of solubilized platelet antigens to thereby produce partially purified platelet antigens; and
    affixing the partially purified platelet antigens to a solid matrix to produce a substrate useful in the detection of antibodies directed against platelet antigens.

3. A method for detecting antibodies directed against platelet antigens in a biological sample, the method comprising the steps of:
    treating platelets with an aqueous solution comprising a substantially removable nonionic detergent to solubilize platelet antigens comprising HLA and platelet-specific antigens and to produce a lysate;
    separating insoluble particles and excess detergent from the lysate so as to minimize detergent interference with binding in subsequent assays by antibodies directed against platelet antigens to platelet antigens and to form a solution;
    contacting said solution with a matrix-bound human IgG to remove from the solution substances nonimmunospecifically binding to the matrix-bound human IgG to thereby produce partially purified platelet antigens;
    affixing the partially purified platelet antigens to a solid matrix;
    contacting said solid matrix with a biological sample possibly containing antibodies against platelet antigens; and
    determining the level of antibody bound to the solid matrix.

4. A method for identification of a platelet source immunologically compatible with a prospective platelet recipient or for the detection of serum antibodies directed towards platelets in a biological sample from a thrombocytopenic individual, the method comprising:
    treating a platelet sample from the platelet source with an aqueous solution comprising a substantially removable nonionic detergent to solubilize platelet antigens comprising HLA and platelet-specific antigens and to produce a lysate;

separating insoluble particles and excess detergent from the lysate so as to minimize interference with binding in subsequent assays by platelet antigens to antibodies directed against platelet antigen and to produce a solution of solubilized platelet antigens;

contacting said solution with matrix-bound human IgG to remove from the solution substances nonimmunospecifically binding to the matrix-bound human IgG to thereby produce partially purified platelet antigens;

attaching the partially purified platelet antigens to a solid matrix to produce affixed partially purified platelet antigens;

obtaining an antibody-containing sample from a pool of previously untransfused male individuals having an AB positive blood type;

identifying a prospective platelet recipient, a thrombocytopenic individual possibly having serum antibodies directed towards platelets;

contacting a first portion of said affixed partially purified platelet antigens with a sample possibly containing antiplatelet antibodies from the prospective platelet recipient or from a thrombocytopenic individual suspected to have antiplatelet antibodies, under conditions facilitating binding of antibody specific for platelet antigens to the affixed partially purified platelet antigens;

contacting a second portion of said affixed partially purified platelet antigens with a sample from the pool of previously untransfused males having an AB positive blood type, under conditions facilitating binding of antibody specific for platelet antigens to the affixed partially purified platelet antigens;

determining a first level of antibody bound to the first portion of the affixed partially purified platelet antigen and a second level of antibody bound to the second portion of the affixed partially purified platelet antigens; and comparing the first level of bound antibody to the second level of bound antibody, a platelet source immunologically compatible with said prospective platelet recipient being identified when said first level is not substantially greater than said second level or the presence of antiplatelet or antibodies in a thrombocytopenic individual being identified when said first level is significantly greater than said second level.

5. The method of claim 1, 3, or 4, wherein the detergent is an alkyl-N-methylglucamide or an alkylglucoside which is sufficiently separable from the solution of solubilized platelet antigens to minimize interference with binding of antibodies directed against platelet antigens to platelet antigens.

6. The method of claim 1, 2, 3 or 4 wherein the detergent is an alkyl-N-methylglucamide.

7. The method of claim 1, 2, 3 or 4 wherein the detergent is decanoyl-N-methylglucamide, nonanoyl-N-methylglucamide, octanoyl-N-methylglucamide or heptanoyl-N-methylglucamide.

8. The method of claim 1, 2, 3 or 4 wherein the detergent is decanoyl-N-methylglucamide.

9. The method of claim 1, 2, 3 or 4 wherein the detergent is n-decyl beta-D-glucopyranoside, n-dodecyl beta-D-glucopyranoside, n-dodecyl beta-D-maltoside, n-heptyl beta-D-glucopyranoside, n-hexyl beta-D-glucopyranoside, n-octyl beta-D-glucopyranoside, n-nonyl beta-D-glucopyranoside or n-octyl alpha-D-glucopyranoside.

10. The method of claim 1, 2, 3 or 4 wherein the aqueous solution comprises between about 0.2% and about 0.5% dialyzable nonionic detergent.

11. The method of claim 1, 2, 3 or 4 wherein the insoluble particles are separated by a step comprising centrifugation.

12. The method of claim 1, 2, 3 or 4 wherein the excess detergent is separated by a step comprising dialysis.

13. The method of claim 1, 2, 3 or 4 wherein the solid matrix is nitrocellulose paper, polystyrene or latex.

14. The method of claim 4 wherein the prospective platelet recipient is refractory to increases in circulating platelet content.

15. A method of preparing a platelet reagent for use in platelet antibody detection assays, the steps comprising:

obtaining a platelet sample;

solubilizing the platelet sample with about 1 mg per mg platelet protein of a non-ionic alkyl-N-methylglucamide or an alkylglucoside detergent for about 30 min at about 0° C. to produce a solubilized platelet sample;

separating insoluble particles and excess detergent from the solubilized platelet sample to minimize interference with binding of antibodies directed against platelet antigens to platelet antigens to form a solution of solubilized platelet antigens comprising HLA and platelet-specific antigens;

contacting said solution with matrix-bound human IgG to absorb substances nonimmunospecifically binding to the matrix-bound human IgG from the solution to thereby produce partially purified solubilized platelet antigens; and binding the partially purified solubilized platelet antigens to an inert matrix to form a platelet reagent for use in subsequent platelet antibody detection assays;

wherein the platelet reagent retains immunoreactivity for at least 100 days in storage.

16. The method of claim 15 wherein the inert matrix is a nitrocellulose solid matrix suitable for a biological sample or assay of antibodies binding to the affixed purified platelet antigens.

17. The method of claim 14 wherein the inert matrix is nitrocellulose paper, polystyrene or latex.

* * * * *

UNITED STATES PATENT AND TRADEMARK OFFICE
CERTIFICATE OF CORRECTION

PATENT NO.  : 4,959,308
DATED       : SEPTEMBER 25, 1990
INVENTOR(S) : OGDEN

It is certified that error appears in the above-identified patent and that said Letters Patent is hereby corrected as shown below:

Col. 17, line 20, "recipient, a throm-" should read recipient, or thromline 49, "antiplatelet or antibodies" should read antiplatelet antibodies.

Col. 18, line 58, "of claim 14 ..." should read of claim 15

Signed and Sealed this

Sixteenth Day of February, 1993

Attest:

STEPHEN G. KUNIN

Attesting Officer    Acting Commissioner of Patents and Trademarks